(12) United States Patent
Couture (10) Patent No.: US 6,540,355 B1
(45) Date of Patent: Apr. 1, 2003

(54) COMPUTERIZED EYE TESTING AND EXERCISES

(76) Inventor: Paul M. Couture, 49 Whitelands House, Cheltenham Terrace, London 5W3 4QY (GB)

(*) Notice: Subject to any disclaimer, the term of this patent is extended or adjusted under 35 U.S.C. 154(b) by 107 days.

(21) Appl. No.: 09/742,907

(22) Filed: Dec. 20, 2000

Related U.S. Application Data (60) Provisional application No. 60/171,692, filed on Dec. 20, 1999.

(51) Int. Cl.$^7$ ................................................ A61B 3/00
(52) U.S. Cl. ...................................................... 351/203
(58) Field of Search ................................. 351/203, 242, 351/243; 342/176, 185; 345/204, 690; 348/578, 678, 61, 68, 69, 70

(56) References Cited

U.S. PATENT DOCUMENTS 3,653,044 A * 3/1972 Breeze et al. ................ 342/185
5,933,130 A * 8/1999 Wagner ........................ 345/690

* cited by examiner

Primary Examiner—George Manuel
(74) Attorney, Agent, or Firm—Jeffrey D. Myers; Peacock, Myers & Adams, P.C.

(57) ABSTRACT

A method, apparatus, and software for exercising human eyes with a monitor onto which is projected a plurality of shapes such that portions of the shapes have a contrast changing at a speed less than or equal to approximately 2.0 cycles/sec. The shapes comprise paired shapes of opposite colors (black/white, red/green, or blue/yellow, or combinations thereof), and the speed is preferably less than or equal to approximately 0.8 cycles/sec. Also a method, apparatus, and software projecting a plurality of symbols each comprising a plurality of bars one of which has a length different than that of others in the symbol. A visual efficiency is calculated based upon a number of identical symbols correctly located by a user and a time to locate the identical symbols.

22 Claims, 7 Drawing Sheets

||||    Press A

|||    Press S

|||    Press D

||||    Press F

|||    Press H

|||    Press J

|||    Press K

||||    Press L

Press A

Press S

Press D

Press F

Press H

Press J

Press K

Press L

Count how many symbols of the folowing type are displayed in the table below and press appropriate button (0 to 9)

COMPUTERIZED EYE TESTING AND EXERCISES

CROSS-REFERENCE TO RELATED APPLICATIONS

This application claims the benefit of the filing of U.S. Provisional Patent Application Ser. No. 60/171,692, entitled "Computerized Eye Training and Exercises", filed on Dec. 20, 1999, and the specification thereof is incorporated herein by reference.

COPYRIGHTED MATERIAL

A portion of the disclosure of this patent document contains material that is subject to copyright protection. The owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

1. Field of the Invention (Technical Field)

The present invention relates to computer hardware and software for testing eyes, exercising eyes, both for proper individualized setup of computer monitors and reduction of eye fatigue.

2. Background Art

More and more persons are subjected to increased use of computer monitors at work, school, and home. Unfortunately, testing of an individual's eyesight in response to such increased use is typically performed in clinical settings, away from the actual work/school/home conditions.

The present invention provides for in-situ testing of eyesight using an actual computer monitor frequented by the user. Accordingly, adjustments to the monitor can be made or suggested to improve conditions for the user. Furthermore, eyesight-training exercises are provided by the invention to provide for in-site exercises to improve user visual acuity and reduce strain and fatigue.

SUMMARY OF THE INVENTION (DISCLOSURE OF THE INVENTION)

The present invention is of a method (and corresponding apparatus and computer software) for exercising human eyes comprising providing a monitor and projecting onto the monitor a plurality of shapes such that portions of the shapes have a contrast changing at a speed less than or equal to approximately 2.0 cycles/sec. In the preferred embodiment, the shapes comprise paired shapes of opposite colors (black/white, red/green, or blue/yellow, or combinations thereof), and the speed is less than or equal to approximately 0.8 cycles/sec. The shapes are preferably triangles, bars, or squares. The contrast preferably changes smoothly, most preferably between approximately 0.02 and 1.0.

The present invention is also of a method (and corresponding apparatus and computer software) for testing human eyes comprising providing a monitor and projecting onto the monitor a plurality of symbols each comprising a plurality of bars one of which has a length different than that of others in the symbol. In the preferred embodiment, a visual efficiency is calculated based upon a number of identical symbols correctly located by a user and a time to locate the identical symbols. Monitor tests are projected to determine monitor settings appropriate to an individual user's eyes. Also projected are monitor tests presenting a shape of changing contrast to test an individual user's eye status at any given time the tests are administered.

A primary object of the present invention is to provide an apparatus and method for automating the setup of monitors for a particular individual's eyes to maximize comfort and minimize eye strain and fatigue.

A primary advantage of the present invention is its ease of incorporation into existing computers and computer-based systems.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS BEST MODES FOR CARRYING OUT THE INVENTION

The present invention is of methods and apparatuses for: (1) individualized setup of monitors for personal comfort and to reduce eye strain and fatigue; (2) vision exercises to reduce eye fatigue; and (3) testing of eye performance and fatigue over time. The preferred embodiment is computer software that provides all the capabilities of the invention in a single package, although smaller packages incorporating subsets are also valuable.

The present invention tests and tracks the potential capabilities of an individual person's visual acuity. It differs from traditional eye clinic approaches because the tests are performed in the sphere of the person's work activities. The invention tests various parameters that most often exist at a computer workstation, creating conditions of testing simulating the conditions of real work activity, including time factors. Additionally, the present invention allows for control of a workstation's conditions based on test results, and provides methods for detecting visual insufficiency in optimal and adverse conditions. The testing procedures do not require any additional equipment beyond a computer and monitor and take little time to perform. The preferred tests comprise what will be referred to as the "Vision Test", the "Monitor Test", and the "Visual Productivity Test".

The tests of the invention are principally designed for: (1) testing loss of vision sharpness caused by intensive usage of visual displays and computer monitors; and (2) testing and adjusting of visual displays and computer monitors to individual user's visual characteristics. The preferred tests comprise what will be referred to as the "Vision Test", the "Monitor Test", and the "Visual Productivity Test".

The present invention also delivers tools and methods allowing a person, based on the test results, to optimize visual work and to do effective exercises aimed at rehabilitation and maintenance of eye performance that are performed at the person's work place. The preferred exercises comprise what will be referred to as the "Zebra Exercise", the "Pyramid Exercise", and the "Chess Exercise".

The exercises of the invention are principally designed for: (1) reducing eye stress and fatigue disorders caused by prolonged and intensive usage of visual displays and computer monitors; (2) restoring vision productivity in view of reductions in optical contrast sensitivity, sight sharpness, and image recognition caused by eye stress and fatigue disorders; (3) preventing the loss of vision productivity caused by prolonged and intensive usage of visual displays and computer monitors during developmental stages particularly prone to eye contrast sensitivity loss; and (4) reducing secondary effects caused by eye stress and fatigue disorders, including loss of concentration, nervousness, headaches, and general fatigue.

The exercises of the invention work on three types of eye exhaustion: (1) muscle weariness; (2) sensor weariness; and (3) vision weariness. The target of the exercises is to remove the four following negative effects: (1) exhaustion in mechanisms of primary organization of a signal (refraction, accommodation, and converging devices); (2) exhaustion in reception mechanisms (processes proceeding in the retina shell); (3) exhaustion in structures of the primary analyzer (processing of signals of the retina); and (4) exhaustion in mechanisms of the central analyzer.

Vision Test

The Vision Test controls the eyesight system via the computer measuring threshold frequency-contrast characteristics. The test is based on using test images as space lattices. Each lattice comprises alternating vertical and horizontal white and black strips of certain width. Contrast between the strips smoothly changes to a perpendicular direction of the strips. The change can be linear (constant speed), logarithmic (speed decreases on approaching maximum contrast), or based on another law such as a sine wave, or a combination thereof. The preferred embodiment employs a linear change and then a logarithmic change as maximum contract is approached. Along strips, contrast does not vary. The tests differ from each other by spatial frequency, i.e., the number of the periods of dark and light strips per unit of a sight field. Preferably, the test employs lattices of five spatial frequencies with a step in one octave (1.25, 2.5, 5.0, 10.0, 20.0 cycles/angle degree). The contrast changes in interval preferably from 0.02 to 0.6 with construction speed of $\frac{1}{50}$ sec.

When the subject distinguishes a lattice, the subject must press a button and the contrast level is then fixed. Every lattice is preferably presented three times. After the session, the invention constructs a chart of the determined contrast frequency characteristics. The subject preferably creates at the work place an ideal test record established when the subject uses the best optical correction (if needed), the most comfortable illumination, and at a time of best physical and psychological status. If a subsequent test at the work place reveals test results that are a give percentage (such as 10%) worse than the ideal record, visual training exercises are called for.

Monitor Test

The Monitor Test generates a visual test, such as that of the Vision Test of the invention, at each quadrant of a monitor and in the center of the monitor. The software of the invention compares results and detects if there are any factors that could worsen a subject's visual perception. If needed, the software generates brief tests and static images for adjusting the monitor. This test also helps to select a proper monitor for a specific user.

Use of the Monitor Test has revealed that LCD monitors tend to worsen users' visual acuity. This happens because an LCD pixel is a strict rectangle and generates additional high frequency video signals that overworks a subject's visual analyzer. As a second example, uncalibrated monitors with different contrast frequency characteristics in different areas and/or for different colors also overworks a subject's visual analyzer and decreases the level of human visual acuity.

Visual Productivity Test

Figure 1:
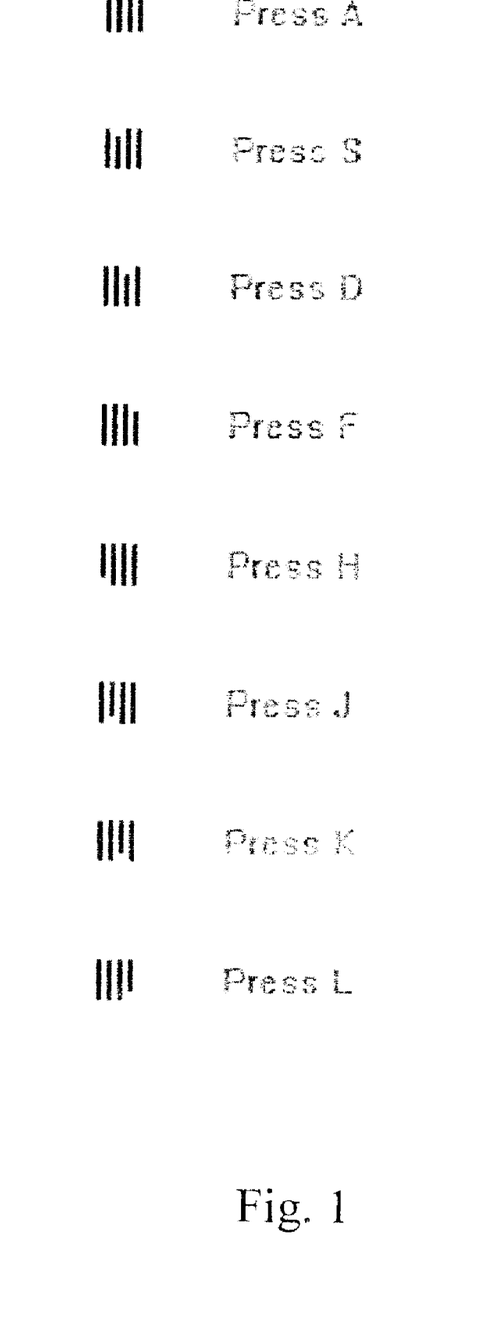
FIGS. 1–3 illustrate the preferred Visual Productivity Test of the invention.
Figure 2:
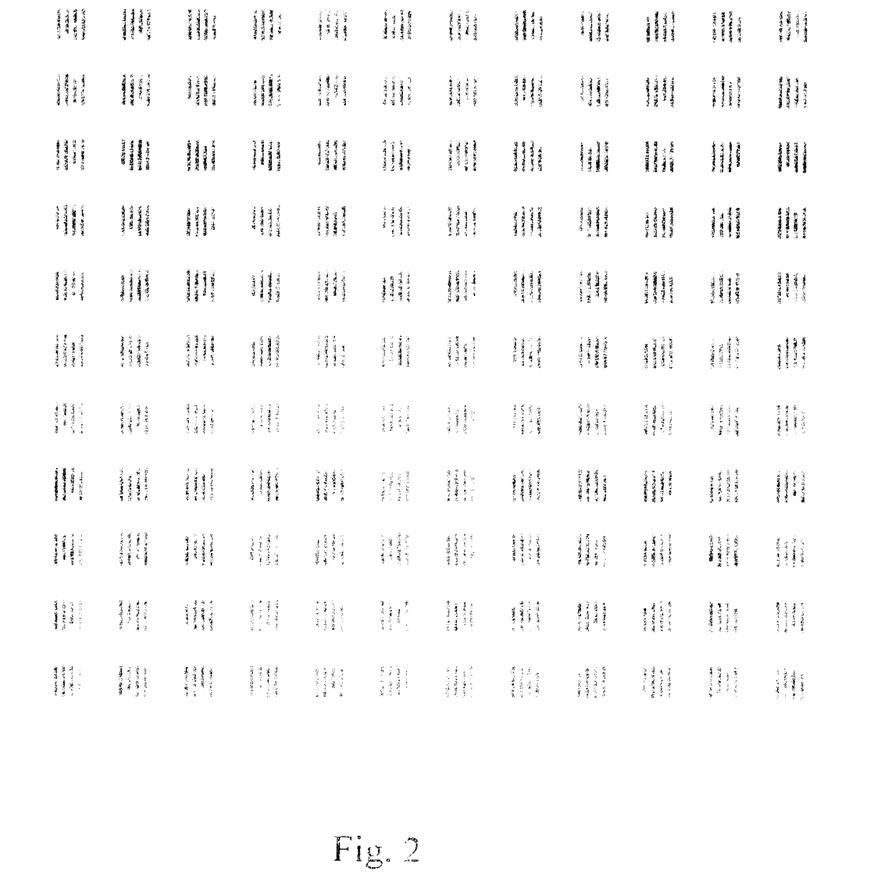
Figure 3:
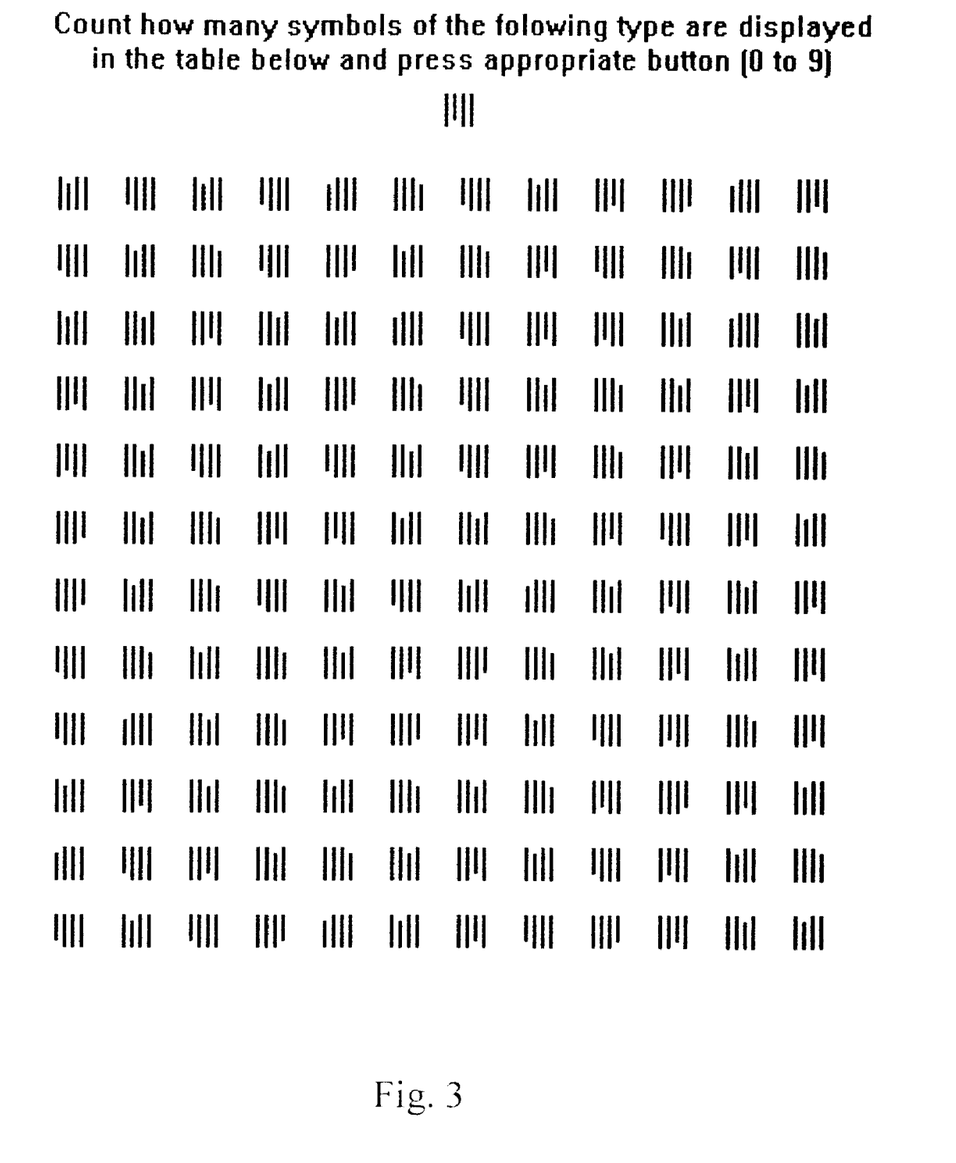

The Visual Productivity Test generates a proof table comprising 8 types of symbols (see FIGS. 1–3). Each symbol comprises 4 parallel lines. One of them is shorter and located variously in relation to others, preferably with 8 variants. This choice corresponds to an optimal number of stimulus gradations recommended by the psychological community (three binary digits (bits) of information). The subject then has to count the number of similar symbols, with visual efficiency being calculated according to the following formula:

$$V=(n/N)\times(n/t)$$

where V is visual efficiency, N is the total number of the symbol chosen, n the number of proper answers, and t the time spent for the test. The first multiplier is the correctness index of the task performance, the second is the speed index of the test performance.

The choice of preferred symbols intentionally steers away from figures, letters, or Landolt rings. The preferred display symbols do not bring superfluous information in a video with a signal that will interfere with the objective work of the visual analyzer. The short line preferably differs on $\frac{1}{5}$ spatial angular degree from the other lines. The space between the lines is preferably 5 spatial angular degrees. Background and contrast is preferably optimized based on preceding visual tests.

Zebra Exercise

Figure 4:
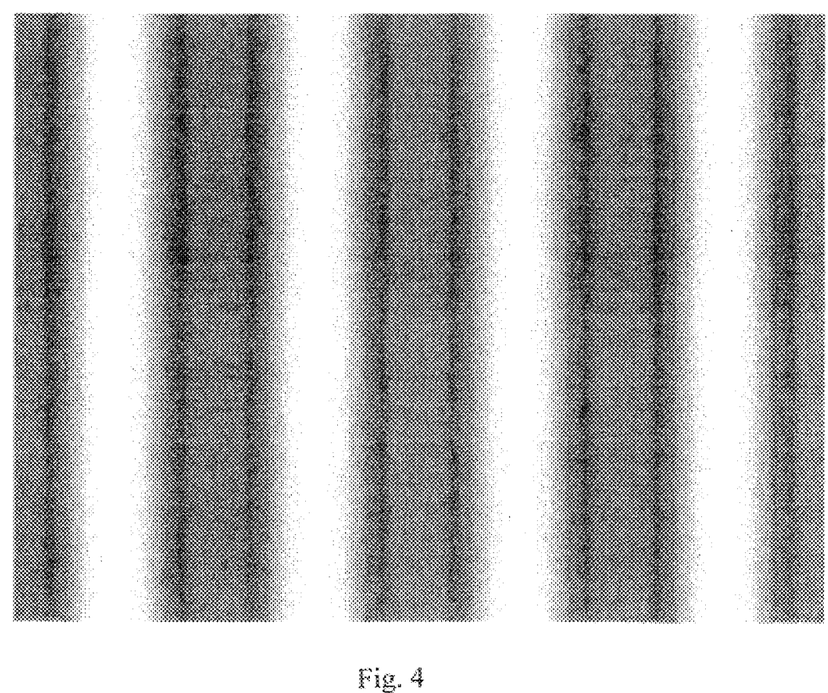
FIGS. 4–5 illustrate the preferred Zebra Exercise of the invention.
Figure 5:
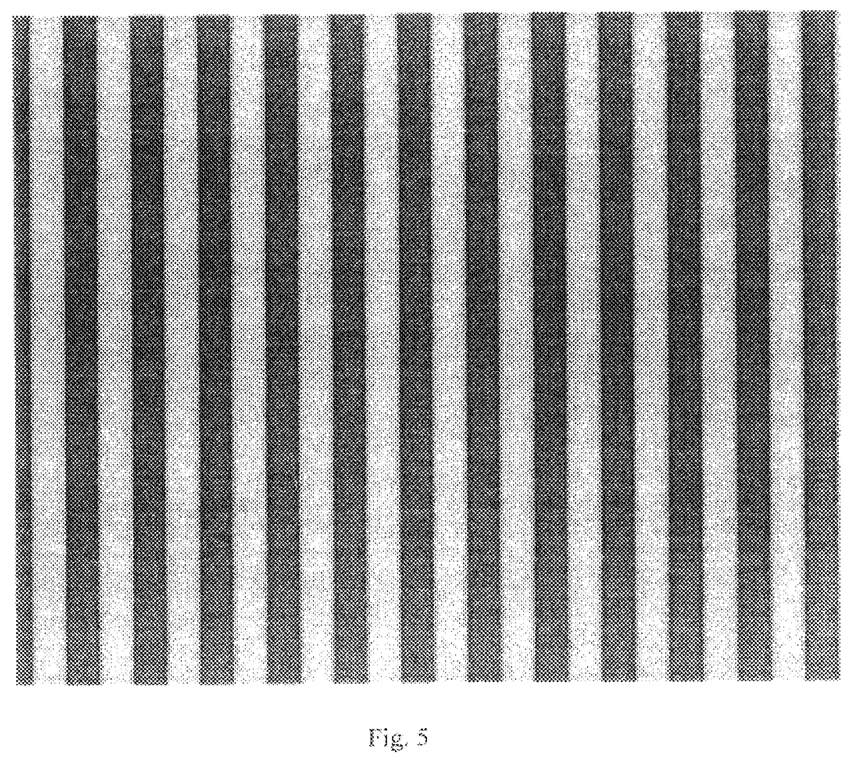

Referring to FIGS. 4–5, the Zebra Exercise is based on using exercise images as space lattices. Each lattice preferably comprises alternating vertical and horizontal white and black strips of certain width. Contrast between the strips smoothly changes to a perpendicular direction of the strips. The change can be linear (constant speed), logarithmic (speed decreases on approaching maximum contrast), or based on another law such as a sine wave, or a combination thereof. The preferred embodiment employs a linear change and then a logarithmic change as maximum contract is approached. Along the strips, contrast does not vary. The exercises differ from each other by a spatial frequency, i.e., the number of the periods of dark and light strips per unit of a sight field. The exercise preferably uses lattices of five spatial frequencies with a step in one octave (e.g., 1.25, 2.5, 5.0, 10.0, 20.0 cycles/angle degree). The contrast preferably changes in interval from 0.02 to 1.0 with the effect of moving the image with a speed less than or equal to 2 cycles/sec. The procedure preferably repeats using opponent colors.

The results of the training are increased eyesight sharpness, improved frequency contrast sensitivity, improved accommodation capacity, improved eye detecting and recognizing capacity, and improved visual productivity. The consecutive presentation of the exercise figures of growing and decreasing angular size allows expansion of a pass band of the visual system and the stimulation of each eye's muscles. This occurs because of the effect of approach and removal of the image and the effect of defocusing of the synthesized image on a retina.

Average accommodation time is 1.3–2.8 seconds, and so the average accommodation speed is 0.5–0.8 cycles/sec. This is why contrast changing with less than or equal speed recovers rhythm of each eye's muscular work. Using a speed of 2.0 cycles/sec or greater is unproductive.

Using figures of opposite colors of different orientation serves for effective stimulation of black/white, red/green, and blue/yellow channels of visual analysis responsible for color detection in the brain. This decreases the spherical and chromatic aberration found in certain clinical cases. Influence of the ophthalmic-impellent muscles is done by removal of a static pressure. This is achieved by using changing of object locations and the point of fixation.

The exercise trains contrast perception using smoothly changing video signals generated by the image in contrast interval from 0.02 up to 1.0 (or other interval as set by a user) according to specific rules. The change can be linear (constant speed), logarithmic (speed decreases on approaching maximum contrast), or based on another law such as a sine wave, or a combination thereof. The preferred embodiment employs a linear change and then a logarithmic change as maximum contract is approached. These exercise dynamic images provide quality regulation of background impulse flow in the neuron net. This means that "nervous" noise in neuron communication nets aligning to "white" (gauss) noise and so improves signal-to-noise ratio in the neuron chain of the visual analyzer. This relaxes and positively influences visual analyzer departments in the brain cortex. As a result, the subject can detect utility of a signal of information flow with greater speed and accuracy. The exercise also results in increased adaptive eye functions and improvement of accommodation activity due to improving the signal-to-noise ratio in the neuron chain of the visual analyzer.

Pyramid Exercise

Figure 6:
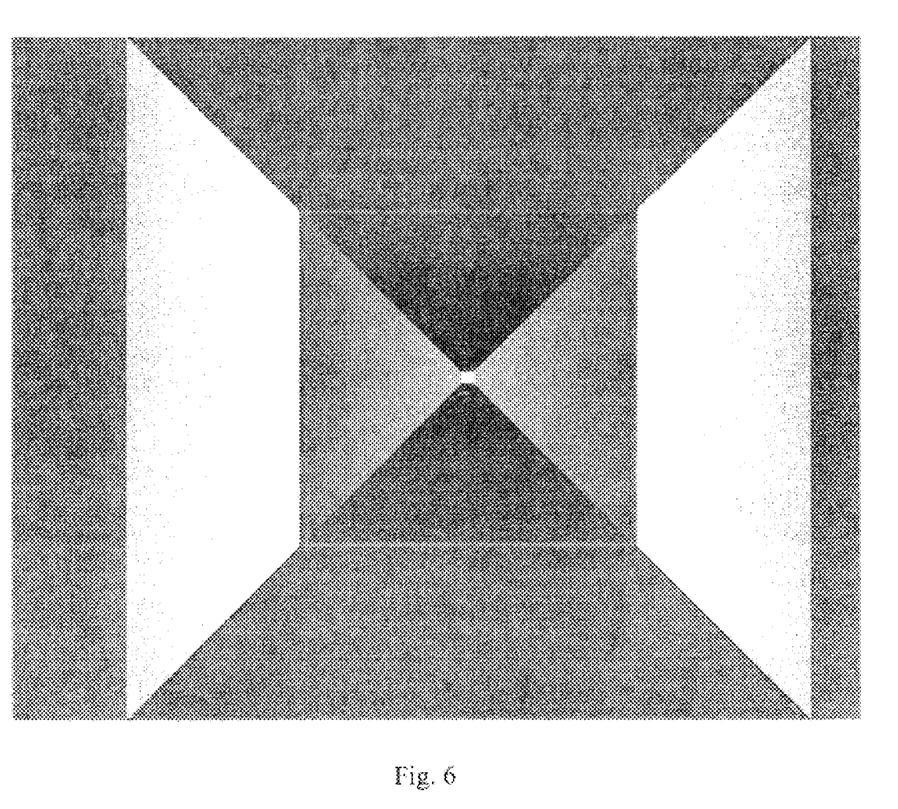
FIG. 6 illustrates the preferred Pyramid Exercise of the invention.

Referring to FIG. 6, the Pyramid Exercise uses as a training object an image of triangles (4, 8, 16, for example) with the bases forming a square and a common apex at the center of the square. Contrast of the structural elements smoothly changes from 0.02 (minimal contrast level) to 1.0 (maximal contrast). The change can be linear (constant speed), logarithmic (speed decreases on approaching maximum contrast), or based on another law such as a sine wave, or a combination thereof. The preferred embodiment employs a linear change and then a logarithmic change as maximum contract is approached. This creates an effect of moving contrast area inside the triangles and the square relative to the center. For creation of this complex dynamic image, the invention preferably uses black-white, red-green, and blue-yellow palettes.

The theory behind the Pyramid Exercise is substantially identical to that behind the Zebra Exercise.

Chess Exercise

Figure 7:
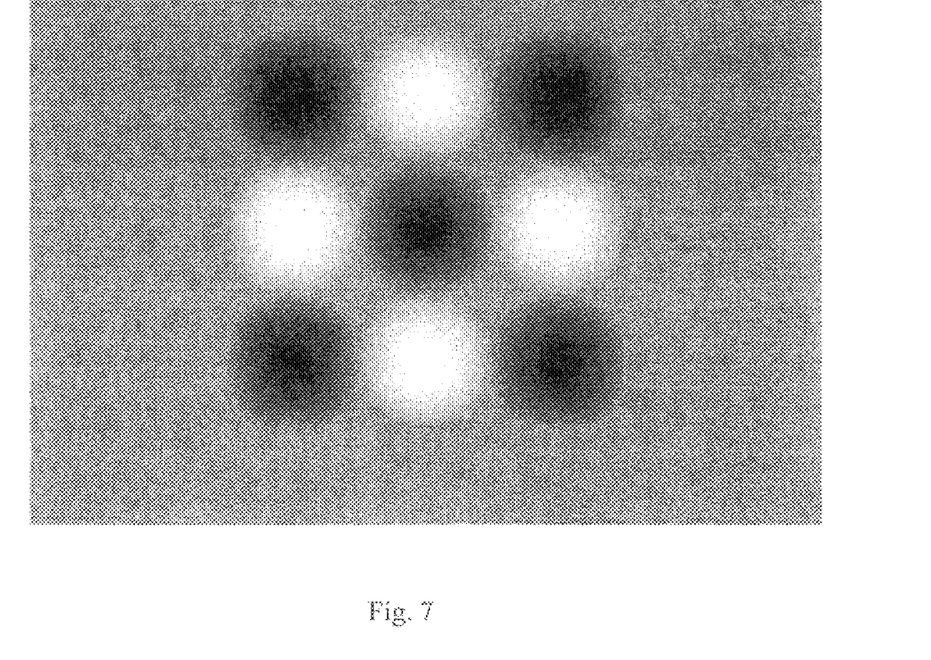
FIG. 7 illustrates the preferred Chess Exercise of the invention.

Referring to FIG. 7, the Chess Exercise provides basic impact images that are chess-board lattices of black-white, red-green, and blue-yellow (opposite) colored squares. The exercise trains contrast perception using smoothly changing video signals generated by elements of the chess-board-like image in contrast interval from 0.02 up to 1.0 with changing angular size relative to the center with a speed of less than or equal to 2.0 cycles/sec. The change can be linear (constant speed), logarithmic (speed decreases on approaching maximum contrast), or based on another law such as a sine wave, or a combination thereof. The preferred embodiment employs a linear change and then a logarithmic change as maximum contract is approached.

The theory behind the Chess Exercise is substantially identical to that behind the Zebra Exercise.

Preferred Software

The invention is preferably embodied in computer software, most preferably operating on an IBM-compatible personal computer running a Windows™ operating system (most preferably Windows98®). A standard cathode ray tube (CRT) monitor is preferably employed rather than a liquid crystal display (LCD) monitor. Profiles can be created, maintained, and updated for individual users. All or a subset of the tests and exercises of the invention may be implemented. A wide variety of options for the tests and exercises are preferably adjustable, such as size of monitor, initial contrast levels, and the like. As may be readily understood, the invention can be implemented on virtually any computer hardware, operating system, and programming language combination.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. An apparatus for exercising human eyes, said apparatus comprising:
    a monitor; and
    a computer projecting onto said monitor a plurality of shapes such that portions of said shapes have a contrast changing at a speed less than or equal to approximately 0.8 cycles/sec.

2. The apparatus of claim 1 wherein said shapes comprise paired shapes of opposite colors, wherein said opposite colors are selected from the group consisting of black/white, red/green, and blue/yellow.

3. The apparatus of claim 1 wherein said shapes are selected from the group consisting of triangles, bars, and squares.

4. The apparatus of claim 1 wherein said contrast changes smoothly.

5. The apparatus of claim 4 wherein said contrast changes smoothly between approximately 0.02 and 1.0.

6. An apparatus for testing human eyes, said apparatus comprising:
    a monitor; and
    a computer projecting onto said monitor a plurality of symbols each comprising a plurality of bars one of which has a length different than that of others in said symbol and wherein said computer additionally calculates a visual efficiency based upon a number of identical symbols correctly located by a user and a time to locate said identical symbols.

7. The apparatus of claim 6 wherein said computer additionally projects onto said monitor tests to determine monitor settings appropriate to an individual user's eyes.

8. The apparatus of claim 6 wherein said computer additionally projects onto said monitor tests presenting a shape of changing contrast to test an individual user's eye status at any given time said tests are administered.

9. Computer software for exercising human eyes, said software comprising means for projecting onto a monitor a plurality of shapes such that portions of said shapes have a contrast changing at a speed less than or equal to approximately 2.0 cycles/sec, wherein said contrast changes smoothly between approximately 0.02 and 1.0.

10. The software of claim 9 wherein said shapes comprise paired shapes of opposite colors, wherein said opposite colors are selected from the group consisting of black/white, red/green, and blue/yellow.

11. The software of claim 9 wherein said speed is less than or equal to approximately 0.8 cycles/sec.

12. The software of claim 9 wherein said shapes are selected from the group consisting of triangles, bars, and squares.

13. Computer software for testing human eyes, said software comprising means for projecting onto a monitor a plurality of symbols each comprising a plurality of bars one of which has a length different than that of others in said symbol, wherein said software additionally comprises means for calculating a visual efficiency based upon a number of identical symbols correctly located by a user and a time to locate said identical symbols.

14. The software of claim 13 wherein said software additionally comprises means for projecting onto the monitor tests to determine monitor settings appropriate to an individual user's eyes.

15. The software of claim 13 wherein said software additionally comprises means for projecting onto the monitor tests presenting a shape of changing contrast to test an individual user's eye status at any given time said tests are administered.

16. A method for exercising human eyes, the method comprising the steps of:

providing a monitor; and projecting onto the monitor a plurality of shapes such that portions of the shapes have a contrast changing at a speed less than or equal to approximately 2.0 cycles/sec and wherein the contrast changes smoothly between approximately 0.02 and 1.0.

17. The method of claim 16 wherein in the projecting step the shapes comprise paired shapes of opposite colors, wherein the opposite colors are selected from the group consisting of black/white, red/green, and blue/yellow.

18. The method of claim 16 wherein in the projecting step the speed is less than or equal to approximately 0.8 cycles/sec.

19. The method of claim 16 wherein in the projecting step the shapes are selected from the group consisting of triangles, bars, and squares.

20. A method for testing human eyes, the method comprising the steps of:

providing a monitor;

projecting onto the monitor a plurality of symbols each comprising a plurality of bars one of which has a length different than that of others in the symbol; and calculating a visual efficiency based upon a number of identical symbols correctly located by a user and a time to locate the identical symbols.

21. The method of claim 20 additionally comprising the step of projecting onto the monitor tests to determine monitor settings appropriate to an individual user's eyes.

22. The method of claim 20 additionally comprising the step of projecting onto the monitor tests presenting a shape of changing contrast to test an individual user's eye status at any given time the tests are administered.

* * * * *